US005597182A

United States Patent [19]
Reber et al.

[11] Patent Number: 5,597,182
[45] Date of Patent: Jan. 28, 1997

[54] PERSONAL HUMAN ANATOMY CARD AND METHODS AND SYSTEMS FOR PRODUCING SAME

[75] Inventors: William L. Reber, Schaumburg, Ill.; Cary D. Perttunen, Shelby Township, Mich.

[73] Assignee: Motorola, Inc., Schaumbrg, Ill.

[21] Appl. No.: 533,825

[22] Filed: Sep. 26, 1995

[51] Int. Cl.$^6$ ................................................. B42D 15/00
[52] U.S. Cl. .............................. 283/67; 283/70; 283/75; 283/900
[58] Field of Search ............................. 283/67, 70, 74, 283/75, 76, 78, 107, 109, 900

[56] References Cited

U.S. PATENT DOCUMENTS

| | | | |
|---|---|---|---|
| 4,619,469 | 10/1986 | Grover | 283/900 |
| 4,632,428 | 12/1986 | Brown | 283/900 X |
| 4,692,394 | 9/1987 | Drexler | 283/900 X |
| 4,852,570 | 8/1989 | Levine | 128/630 |
| 5,002,062 | 3/1991 | Suzuki | 128/696 |
| 5,161,826 | 11/1992 | Van Giesen et al. | 283/77 |
| 5,193,855 | 3/1993 | Shamos | 283/900 X |
| 5,325,294 | 6/1994 | Keene | 364/413.01 |

*Primary Examiner*—Willmon Fridie, Jr.
*Attorney, Agent, or Firm*—Bruce E. Stuckman; Jeffrey G. Toler

[57] ABSTRACT

A personal anatomy card includes a card member and a machine-readable storage medium integrated in the card member. Machine-readable data including compressed data representative of a three-dimensional model of a portion of the individual is stored on the machine-readable storage medium. The three-dimensional model is formed by tomographically creating a plurality of two-dimensional cross-sectional images of a portion of the individual, processing the plurality of two-dimensional cross-sectional images to form data representative of the three-dimensional model, and compressing the data to form the compressed data. Optionally, a three-dimensional data player is integrated in the card member. The three-dimensional data player includes a display device, a user interface, and a processor. The processor is operative to decode the compressed data in dependence upon navigation instructions received by the user interface to command the display device to display a selected portion of the three-dimensional model.

26 Claims, 5 Drawing Sheets

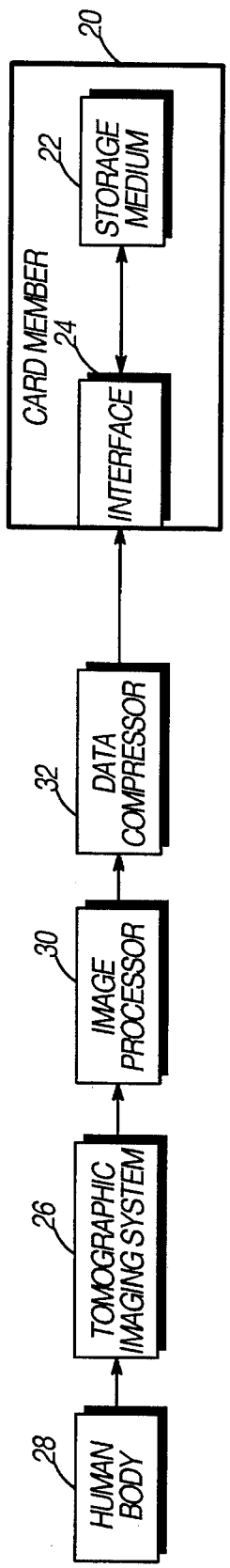
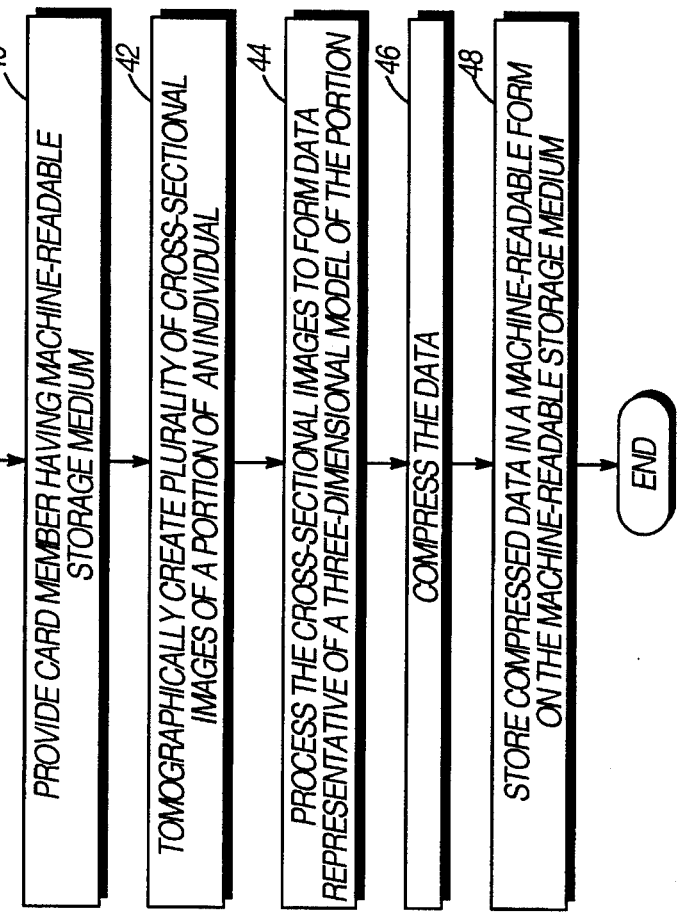

5,597,182

PERSONAL HUMAN ANATOMY CARD AND METHODS AND SYSTEMS FOR PRODUCING SAME

FIELD OF THE INVENTION

The present invention relates to personal medical information cards.

BACKGROUND OF THE INVENTION

In the area of health care, there is a growing need for efficiently storing individuals' medical files for accessing by health-care-related personnel and insurance companies. For example, in an emergency situation in which communication with a patient is either impaired or impossible, it is desired that the patient have a medical information card carried on himself/herself which can be read by emergency medical personnel. U.S. Pat. No. 4,632,428 to Brown discloses a data card providing a microfilmed medical history, eye-readable emergency-oriented personal and medical data, and access to a central medical records bank.

Cards which include both visual medical information and visual identity information are also in existence. U.S. Pat. No. 5,161,826 to Van Giesen et al. discloses a card having the name of a person, an indication of a type of surgery performed on the person, and a surgeon's name on one side of the card. On a reverse side are photographs of the person's head and an X-ray of the surgery on the person. This card allows the person to present proof of a presence of metal within the person's body if an alarm signal is actuated by an X-ray scanning machine, such as one used in airports.

Also, it is envisioned that a number of medical centers will become centers of excellence for their specialties. Each of these medical centers would serve a large geographic area, and perhaps, the entire world population by electronically receiving a patient's medical information from a remote location, performing a diagnosis based on the information, and recommending a treatment based on the diagnosis.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

FIG. 1 is a block diagram of a system for producing a human anatomy card in accordance with the present invention;

FIG. 2 is a flow chart of an embodiment of a method of producing a human anatomy card;

DETAILED DESCRIPTION OF A PREFERRED EMBODIMENT

Figure 3:
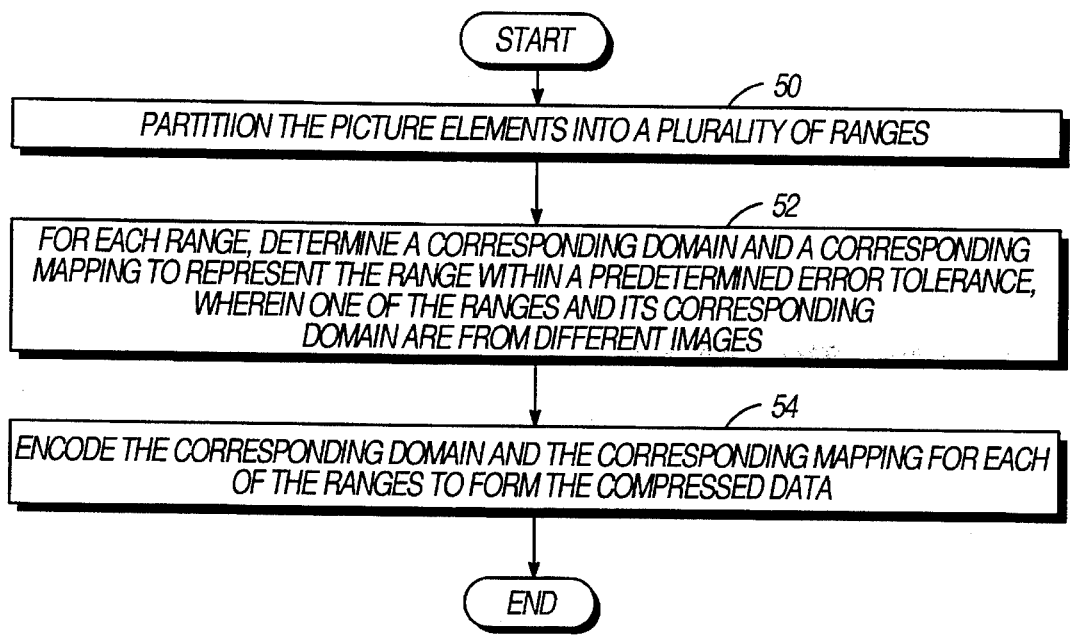
FIG. 3 is a flow chart of a two-dimensional fractal compression method for use in embodiments of the present invention.

Embodiments of the present invention advantageously provide a personal human anatomy card containing a compressed three-dimensional model of an individual's anatomy. The compressed three-dimensional model is viewed using a data player which is either external to the card or integrated in the card. By storing a three-dimensional model of the individual, the personal human anatomy card can be used in both medical treatment and personal identification applications.

FIG. 1 is a block diagram of a system for producing a human anatomy card in accordance with the present invention. The personal human anatomy card includes a card member 20 which, preferably, is sized for carrying on the individual. For example, the card member 20 can be the size of a credit card for carrying within a wallet, a purse, or a pocket of the individual.

A machine-readable storage medium 22 is integrated in the card member 20. The machine-readable storage medium 22 is utilized to store human anatomy information of the individual. The machine-readable storage medium 22 can be in the form of an electronic memory device, a magnetic memory device, or an optical memory device, for example. Preferably, the machine-readable storage medium 22 is non-volatile so that a powering signal need not be applied to maintain the human anatomy information therein. Further, it is preferred that the machine-readable storage medium 22 be rewriteable so that the human anatomy information can be updated.

Also integrated within the card member 20 is an interface 24. The interface 24 is utilized to communicate the human anatomy information between the machine-readable storage medium 22 and an exterior read/write device such as a computer.

A tomographic imaging system 26 is provided to create a plurality of two-dimensional cross-sectional images of a portion of the individual's body 28. The plurality of two-dimensional cross-sectional images are taken at a plurality of depths along a predetermined axis through the individual's body 28. The tomographic imaging system 26 can utilize magnetic resonance imaging (MRI), ultrasound (US), computerized axial tomography (CAT), positron emission tomography (PET), or single photon emission computerized tomography (SPECT), for example, to create the two-dimensional cross-sectional image of thin slices of the individual's body 28 normal to the predetermined axis. It is noted, however, that other modes of tomographic imaging are within the scope of the present invention.

An image processor 30 processes the plurality of two-dimensional cross-sectional images to form data representative of the three-dimensional model. The three-dimensional model can be formed by a plurality of picture elements, or pixels, from each of the plurality of two-dimensional cross-sectional images. Alternatively, the three-dimensional model can be formed by a plurality of volume elements, or voxels, which are produced by stacking the two-dimensional cross-sectional images.

Regardless of the form the three-dimensional model, it is preferred that the image processor 30 first segment the two-dimensional cross-sectional images to isolate a plurality of anatomical objects. In general, the anatomical objects can be any constituent region or part of interest within the images. In practice, the anatomical objects are subimages of members of the individual's body 28, such as bones and organs.

A data compressor 32 compresses the data formed by the image processor 30 to form compressed data representative of the three-dimensional model of the portion of the individual. The compressed data is stored as machine-readable data on the machine-readable storage medium 22 via the interface 24.

The image processor 30 and the data compressor 32 can be embodied by individual processing components. Alternatively, the image processor 30 and the data compressor 32 can be realized by a single computer or like programmable apparatus having a processor and a memory. The actions of the computer are directed by a computer program containing a series of program steps. The computer program can be in the form of either software or firmware.

FIG. 2 is a flow chart of an embodiment of a method of producing a human anatomy card. The method includes a step of providing the card member 20 having the machine-readable storage medium 22 integrated therein, as indicated by block 40. The card member 20 having the machine-readable storage medium 22 can be provided by a PCMCIA card or a smart card, for example.

As indicated by block 42, a step of tomographically creating a plurality of two-dimensional cross-sectional images of a portion of the individual is performed using the tomographic imaging system 26. This step includes scanning at least a portion of individual's body 28 by performing a CAT scan, MRI scan, US scan, PET scan, or SPECT scan, for example. If desired, the entire body can be scanned.

A step of processing the plurality of two-dimensional cross-sectional images, as indicated by block 44, is performed using the image processor 30. The step of processing is performed to form data representative of a three-dimensional model of the portion of the individual. The step of processing can include segmenting the plurality of two-dimensional cross-sectional images to isolate a plurality of anatomical objects. Based upon the anatomical objects which are isolated, the step of processing can include forming the three-dimensional model based on at least one of the anatomical objects.

As indicated by block 46, the data compressor 32 performs a step of compressing the data to form compressed data representative of the three-dimensional model. Preferably, a fractal compression algorithm is utilized in the data compressor 32 to perform the step of compressing. Various fractal compression algorithms, such as those described in U.S. Pat. Nos. 4,941,193, 5,065,447, and 5,347,600, can be utilized to form the compressed data.

A step of storing the compressed data in a machine-readable form on the machine-readable storage medium 22 is performed, as indicated by block 48. The compressed data can be communicated to the machine-readable storage medium 22 via the interface 24.

FIG. 3 is a flow chart of a two-dimensional fractal compression method for use in embodiments of the present invention. Here, the three-dimensional model includes a plurality of picture elements, or pixels, from the plurality of two-dimensional cross-sectional images.

As indicated by block 50, a step of partitioning the plurality of picture elements into a plurality of ranges is performed. The picture elements can be partitioned using quadtree partitioning, HV partitioning, triangular partitioning, or other partitioning methods utilized in fractal compression.

For each range of the plurality of ranges, a step of determining a corresponding domain of the plurality of picture elements and a corresponding mapping to represent the range within a predetermined error tolerance is performed as indicated by block 52. The predetermined error tolerance is based upon a predetermined metric, such as a root-mean square (RMS) metric or a supremum metric, which measures the difference between the range and the representation of the range by the corresponding mapping and domain.

As a modification to basic fractal compression algorithms, the domain corresponding to a range is not necessarily selected from picture elements within the same image as the range. Hence, one of the plurality of ranges and its corresponding domain can be from different ones of the plurality of two-dimensional cross-sectional images. For example, a range from an image taken at a first depth along the predetermined axis can have a domain selected from a similar portion of from another depth. This "inter-image" approach to fractal compression is beneficial in exploiting axial self-similarity of human anatomical objects.

As indicated by block 54, a step of encoding the corresponding domain and the corresponding mapping for each of the plurality of ranges is performed to form the compressed data.

Figure 4:
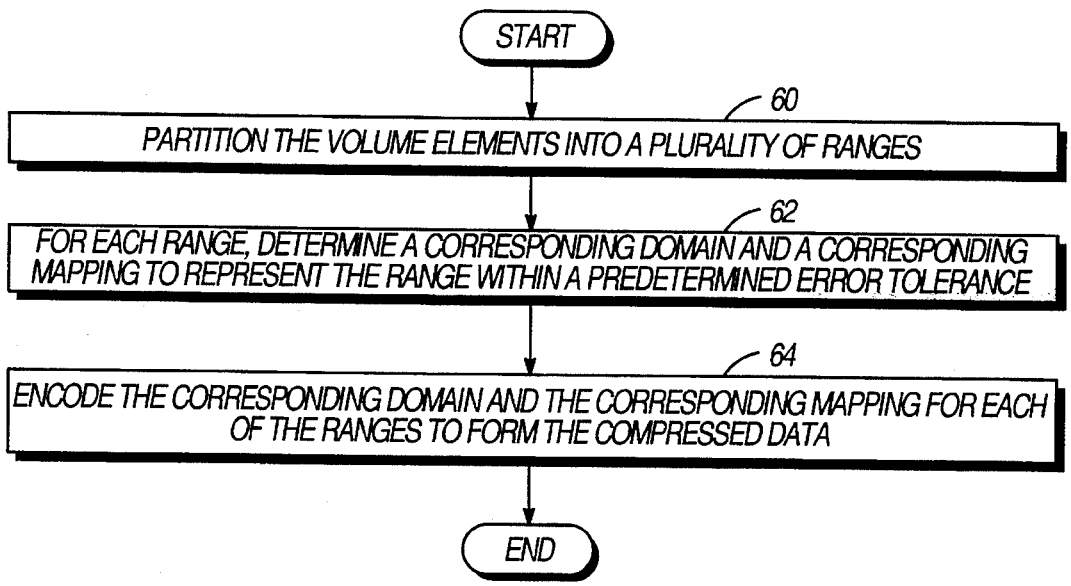
FIG. 4 is a flow chart of a three-dimensional fractal compression method for use in embodiments of the present invention.

FIG. 4 is a flow chart of a three-dimensional fractal compression method for use in embodiments of the present invention. This method can be utilized by the data compressor 32 for a three-dimensional model formed by a plurality of volume elements, or voxels.

As indicated by block 60, a step of partitioning the plurality of volume elements into a plurality of ranges is performed. The ranges can be partitioned into cubes using an octotree partition similar to the two-dimensional quadtree partition. Here, each cube is recursively subdivided into eight subcubes of equal size until the predetermined error tolerance is attained for a corresponding mapping and a corresponding domain.

For each range of the plurality of ranges, a step of determining a corresponding domain of the plurality of volume elements and a corresponding mapping to represent the range within a predetermined error tolerance is performed, as indicated by block 62. As indicated by block 64, a step of encoding the corresponding domain and the corresponding mapping is performed for each of the plurality of ranges to form the compressed data.

This three-dimensional approach to fractal compression is beneficial in exploiting three-dimensional self-similarity of human anatomical objects to form the compressed data.

Figure 5:
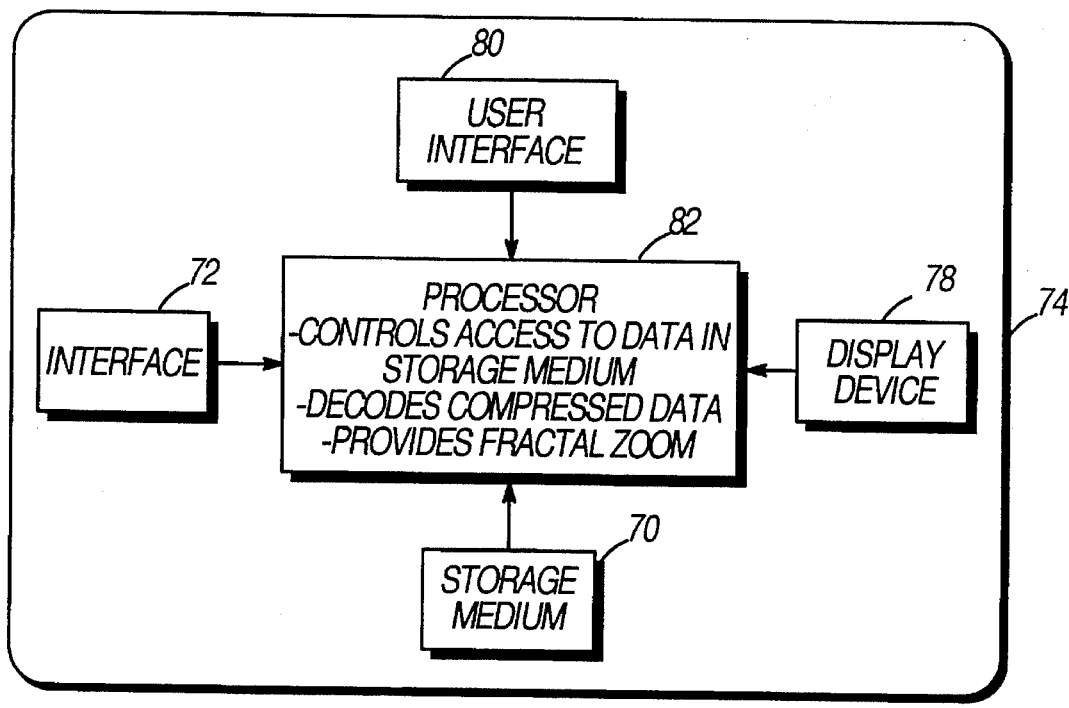
FIG. 5 is a block diagram of a second embodiment of a human anatomy card.

FIG. 5 is a block diagram of a second embodiment of a human anatomy card. Similar to the embodiment of FIG. 1, the human anatomy card includes a storage medium 70 and an interface 72 integrated within a card member 74.

In addition, a three-dimensional data player 76 for navigating the three-dimensional model stored in the storage medium 70 is also integrated in the card member 74. The three-dimensional data player 76 includes a display device 78, a user interface 80, and a processor 82 all integrated in the card member 74. The processor 82 is operative to decode the compressed data of the three-dimensional model stored in the storage medium 70. The compressed data is decoded in dependence upon navigation instructions received by the user interface 80. The processor 82 then commands the display device 78 to display a selected portion of the three-dimensional model in accordance with the navigation instructions.

The processor 82 decodes the compressed data in accordance with decoder software or firmware. The decoding routine can be stored within the processor 82 or in the storage medium 70.

As stated earlier, it is preferred that the compressed data be formed using a fractal compression algorithm. Here, the processor 82 operates as a fractal decoder using a predetermined fractal decoding algorithm. By using fractal compression and decompression, the three-dimensional data player 76 can provide a fractal zoom of the three-dimensional model.

In addition, the processor 82 controls access of the compressed data stored in the storage medium 70. More specifically, the processor 82 is operative to limit the compressed data which is displayed on the display device 78 and limit the compressed data which is communicated to an external device via the interface 72.

To produce the second embodiment of the human anatomy card, a step of integrating the three-dimensional data player 76 in the card member 74 is performed in addition to the steps illustrated in FIG. 2. This step can include integrating the display device 78, the user interface 80, and the processor 82 in the card member 74. This step can further include storing decoder software either in the processor 82 or the storage medium 70.

Figure 6:
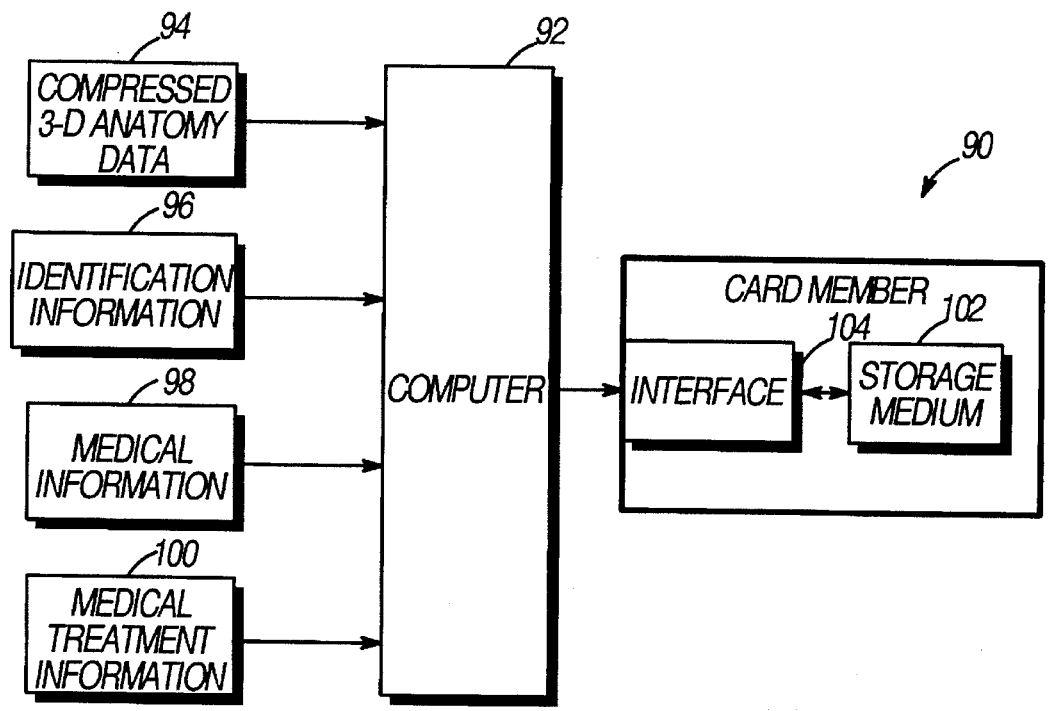
FIG. 6 is a block diagram illustrating a system for storing additional information in a human anatomy card

FIG. 6 is a block diagram illustrating a system for storing additional information in a human anatomy card 90. A computer 92 or like programmable apparatus receives or forms compressed three-dimensional anatomy data 94, additional individual identification information 96 (such as name, social security number, or insurance number), medical information 98, and medical treatment information 100. The computer 92 stores this information in a storage medium 102 interfaced to the computer 92 via an interface 104.

This system is amenable to a PCMCIA embodiment of the human anatomy card 90, wherein the interface 104 is a PCMCIA interface. Here, the human anatomy card 90 can be formed simply by a PCMCIA memory card which is received in a PCMCIA port on the computer 92. Alternatively, the human anatomy card 90 can have a PCMCIA interface along with a three-dimensional data player 76 as illustrated in FIG. 5.

Figure 7:
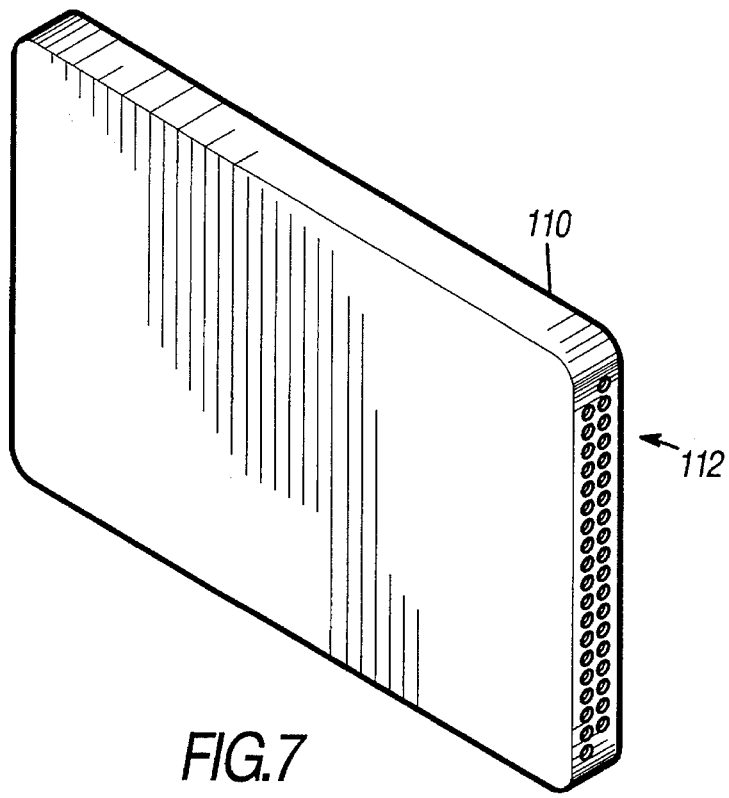
FIG. 7 is an exterior illustration of an embodiment of the human anatomy card.

FIG. 7 is an exterior illustration of a PCMCIA embodiment of the human anatomy card. The human anatomy card includes a card member 110 having a PCMCIA interface 112. A storage medium (not illustrated) such as a memory is integrated within the card member 110.

Figure 8:
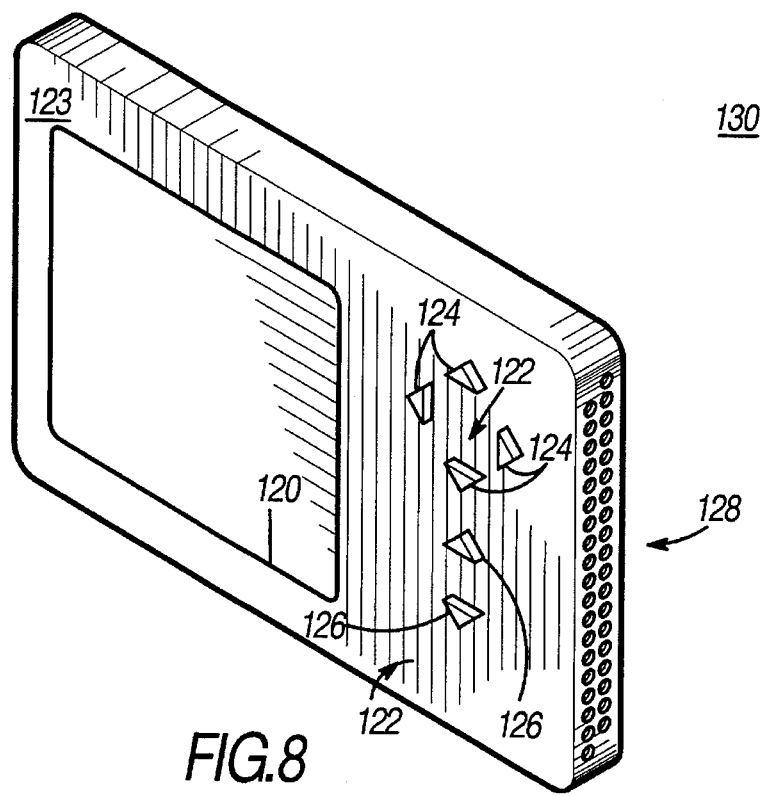
FIG. 8 is an exterior illustration of the second embodiment of the human anatomy card.

FIG. 8 is an exterior illustration of the second embodiment of the human anatomy card. A display device 120, such as a liquid crystal display, and a user interface 122, such as a series of buttons, is integrated in a card member 123. The user interface 122 includes a plurality of buttons 124 for receiving navigation instructions for modifying a perspective of a displayed portion of the three-dimensional model. A second plurality of buttons 126 are included in the user interface 122 for zooming in or out the displayed portion of the three-dimensional model. As illustrated, the personal human anatomy card 130 includes a PCMCIA interface 128 for communicating data with an external device.

Figure 9:
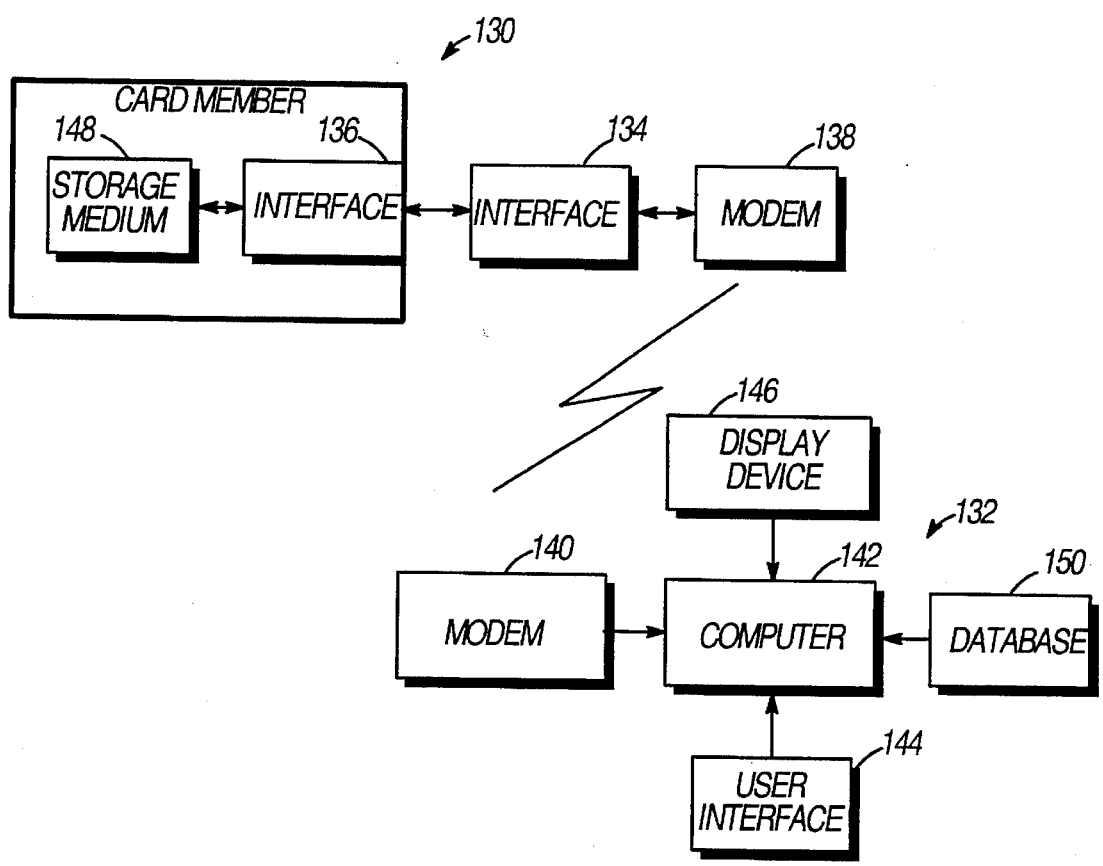
FIG. 9 is a block diagram illustrating a system for remotely accessing a personal human anatomy card.

FIG. 9 is a block diagram illustrating a system for remotely accessing a personal human anatomy card 130. The human anatomy card 130 communicates with an on-line system 132. The on-line system 132 provides remote access and decoding of a three-dimensional model of an individual's anatomy.

The personal human anatomy card 130 is received by an interface 134. The interface 134 mates with an interface 136 within the personal human anatomy card 130. A modem 138 is coupled to the interface 136 to communicate data with a remote modem 140. The remote modem 140 provides communicates the data to a computer system having a computer 142, a user interface 144 (e.g. a keyboard and/or a mouse), and a display device 146 (e.g. a computer monitor).

The on-line system 132 can be utilized by medical personnel distant from the individual to diagnose his/her condition. The medical personnel can navigate a three-dimensional model of the individual stored in a storage medium 148 as follows. Navigation instructions are entered into the user interface 144 by the medical personnel. The navigation instructions are communicated to the personal human anatomy card 130 by the remote modem 140, the modem 138, and the interface 134. In response thereto, the personal human anatomy card 130 communicates the compressed data to the computer 142 by the interface 134, the modem 138, and the remote modem 140. The computer 142 includes decompression software to command the display device 146 to display a selected portion of the three-dimensional model.

Alternatively, a predetermined amount of the compressed data can be transmitted to the computer 142 independent of the navigation instructions. The computer 142 stores the compressed data for decompression and display based upon the navigation instructions received via the user interface 144.

The on-line system 132 can also be utilized for remote identification purposes. Here, the on-line system 132 contains a database 150 of anatomy information for a plurality of individuals, and compares anatomy information received from the human anatomy card 130 thereto. The on-line system 132 can also be utilized to store updates of an individual's anatomy over his/her lifetime.

Thus, there has been described herein a concept, as well as several embodiments including preferred embodiments of a personal human anatomy card and a method and system of producing the same.

Because the various embodiments of the present invention store a three-dimensional model of an individual's anatomy in a card which can be carried by the individual, they provide a significant improvement in that the card can be used both for identification purposes and for medical purposes.

Additionally, the various embodiments of the present invention as herein-described utilize a fractal compression scheme which exploits either the self-similarity exhibited in human anatomical objects to efficiently store the three-dimensional model on a storage medium within the card.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. A method of producing a personal human anatomy card for an individual, the method comprising the steps of:

(a) providing a card member having a machine-readable storage medium integrated therein;

(b) tomographically creating a plurality of two-dimensional cross-sectional images of a portion of the individual;

(c) processing the plurality of two-dimensional cross-sectional images to form data representative of a three-dimensional model of the portion of the individual;

(d) compressing the data to form compressed data representative of the three-dimensional model; and (e) storing the compressed data in a machine-readable form on the machine-readable storage medium of the card member.

2. The method of claim 1 further comprising the step of integrating a three-dimensional data player in the card member, the three-dimensional data player for navigating the three-dimensional model.

3. The method of claim 2 wherein the step of integrating the three-dimensional data player includes integrating a display device, a user interface, and a processor in the card member, the processor operative to decode the compressed data in dependence upon navigation instructions received by the user interface to command the display device to display a selected portion of the three-dimensional model.

4. The method of claim 2 wherein the data is compressed in step (d) using a fractal compression algorithm, and wherein the three-dimensional data player provides a fractal zoom of the three-dimensional model.

5. The method of claim 1 wherein step of processing includes:

segmenting the plurality of two-dimensional cross-sectional images to isolate a plurality of anatomical objects; and forming the three-dimensional model based on at least one of the plurality of anatomical objects.

6. The method of claim 1 wherein the three-dimensional model formed in step (c) includes a plurality of volume elements, and wherein the step of compressing includes:

partitioning the plurality of volume elements into a plurality of ranges;

for each range of the plurality of ranges, determining a corresponding domain of the plurality of volume elements and a corresponding mapping to represent the range within a predetermined error tolerance; and encoding the corresponding domain and the corresponding mapping for each of the plurality of ranges to form the compressed data.

7. The method of claim 1 wherein the three-dimensional model formed in step (c) includes a plurality of picture elements from the plurality of two-dimensional cross-sectional images, and wherein the step of compressing includes:

partitioning the plurality of picture elements into a plurality of ranges;

for each range of the plurality of ranges, determining a corresponding domain of the plurality of picture elements and a corresponding mapping to represent the range within a predetermined error tolerance, wherein one of the plurality of ranges and its corresponding domain are from different ones of the plurality of two-dimensional cross-sectional images; and encoding the corresponding domain and the corresponding mapping for each of the plurality of ranges to form the compressed data.

8. The method of claim 1 further comprising the step of storing identification information in a machine-readable form on the machine-readable storage medium, the identification information for identifying the individual.

9. The method of claim 1 wherein the card member includes a PCMCIA card.

10. The method of claim 1 wherein the card member is sized for carrying on the individual.

11. A personal human anatomy card for an individual, the personal human anatomy card comprising:

a card member;

a machine-readable storage medium integrated in the card member; and machine-readable data stored on the machine-readable storage medium, the machine-readable data including compressed data representative of a three-dimensional model of a portion of the individual formed by:

tomographically creating a plurality of two-dimensional cross-sectional images of a portion of the individual;

processing the plurality of two-dimensional cross-sectional images to form three-dimensional data representative of the three-dimensional model; and compressing the three-dimensional data to form the compressed data.

12. The personal human anatomy card of claim 11 further comprising a three-dimensional data player integrated in the card member, the three-dimensional data player for navigating the three-dimensional model.

13. The personal human anatomy card of claim 12 wherein the three-dimensional data player includes a display device, a user interface, and a processor all integrated in the card member, the processor operative to decode the compressed data in dependence upon navigation instructions received by the user interface to command the display device to display a selected portion of the three-dimensional model.

14. The personal human anatomy card of claim 12 wherein the three-dimensional data is compressed using a fractal compression algorithm, and wherein the three-dimensional data player provides a fractal zoom of the three-dimensional model.

15. The personal human anatomy card of claim 11 wherein processing the plurality of two-dimensional cross-sectional images includes:

segmenting the plurality of two-dimensional cross-sectional images to isolate a plurality of anatomical objects; and forming the three-dimensional model based on at least one of the plurality of anatomical objects.

16. The personal human anatomy card of claim 11 wherein the three-dimensional model includes a plurality of volume elements, and wherein compressing the data includes:

partitioning the plurality of volume elements into a plurality of ranges;

for each range of the plurality of ranges, determining a corresponding domain of the plurality of volume elements and a corresponding mapping to represent the range within a predetermined error tolerance; and encoding the corresponding domain and the corresponding mapping for each of the plurality of ranges to form the compressed data.

17. The personal human anatomy card of claim 11 wherein the three-dimensional model includes a plurality of picture elements from the plurality of two-dimensional cross-sectional images, and wherein compressing the data includes:

partitioning the plurality of picture elements into a plurality of ranges;

for each range of the plurality of ranges, determining a corresponding domain of the plurality of picture elements and a corresponding mapping to represent the range within a predetermined error tolerance, wherein one of the plurality of ranges and its corresponding domain are from different ones of the plurality of two-dimensional cross-sectional images; and encoding the corresponding domain and the corresponding mapping for each of the plurality of ranges to form the compressed data.

18. The personal human anatomy card of claim 11 wherein the machine-readable data includes identification information for identifying the individual.

19. The personal human anatomy card of claim 11 wherein the card member includes a PCMCIA card.

20. The personal human anatomy card of claim 11 wherein the card member is sized for carrying on the individual.

21. A system for producing a personal human anatomy card for an individual, the system comprising:

a tomographic imaging system which tomographically creates a plurality of two-dimensional cross-sectional images of a portion of the individual;

an image processor which processes the plurality of two-dimensional cross-sectional images to form data representative of a three-dimensional model of the portion of the individual;

a data compressor which compresses the data to form compressed data representative of the three-dimensional model; and means for storing the compressed data in a machine-readable form on a machine-readable storage medium integrated in a card member.

22. The system of claim 21 wherein the image processor is operative to segment the plurality of two-dimensional cross-sectional images to isolate a plurality of anatomical objects, and form the three-dimensional model based on at least one of the plurality of anatomical objects.

23. The system of claim 21 wherein the three-dimensional model formed by the image processor includes a plurality of volume elements, and wherein the data compressor performs the steps of:

partitioning the plurality of volume elements into a plurality of ranges;

for each range of the plurality of ranges, determining a corresponding domain of the plurality of volume elements and a corresponding mapping to represent the range within a predetermined error tolerance; and encoding the corresponding domain and the corresponding mapping for each of the plurality of ranges to form the compressed data.

24. The system of claim 21 wherein the three-dimensional model formed by the image processor includes a plurality of picture elements from the plurality of two-dimensional cross-sectional images, and wherein the data compressor performs the steps of:

partitioning the plurality of picture elements into a plurality of ranges;

for each range of the plurality of ranges, determining a corresponding domain of the plurality of picture elements and a corresponding mapping to represent the range within a predetermined error tolerance, wherein one of the plurality of ranges and its corresponding domain are from different ones of the plurality of two-dimensional cross-sectional images; and encoding the corresponding domain and the corresponding mapping for each of the plurality of ranges to form the compressed data.

25. The system of claim 21 further comprising means for storing identification information in a machine-readable form on the machine-readable storage medium, the identification information for identifying the individual.

26. The system of claim 21 wherein the card member includes a PCMCIA card.

* * * * *